（12) United States Patent
Aytar et al.

(10) Patent No.: US 11,254,679 B2
(45) Date of Patent: Feb. 22, 2022

(54) **PROCESS FOR THE PREPARATION OF N-((1R,2S,5R)-5-(*TERT*-BUTYLAMINO)-2-((S)-3-(7-*TERT*-BUTYLPYRAZOLO[1,5-A][1,3,5]TRIAZIN-4-YLAMINO)-2-OXO-PYRROLDIN-1-YL)CYCLOHEXYL) ACETAMIDE**

(71) Applicant: BRISTOL-MYERS SQUIBB COMPANY, Princeton, NJ (US)

(72) Inventors: Burcu Selin Aytar, Monroe, NJ (US); Alina Borovika, Brooklyn, NY (US); Collin Chan, New York, NY (US); Joerg Deerberg, Columbus, NJ (US); Nathan R. Domagalski, Niantic, CT (US); Martin D. Eastgate, Titusville, NJ (US); Yu Fan, Highland Park, NJ (US); Michael David Bengt Fenster, New York, NY (US); Robert V. Forest, Hillsborough, NJ (US); Francisco Gonzalez-Bobes, Hillsborough, NJ (US); Rebecca A. Green, Metuchen, NJ (US); Matthew R. Hickey, Yardley, PA (US); Nathaniel David Kopp, Newtown, PA (US); Thomas E. La Cruz, Flemington, NJ (US); Kathleen Lauser, Minneapolis, MN (US); Hong Geun Lee, Seoul (KR); David K. Leahy, Hightstown, NJ (US); Helen Y. Luo, San Francisco, CA (US); Thomas M. Razler, Yardley, PA (US); Scott A. Savage, Yardley, PA (US); Chris Sfouggatakis, Staten Island, NY (US); Maxime C. D. Soumeillant, Princeton, NJ (US); Serge Zaretsky, Fords, NJ (US); Bin Zheng, Kendall Park, NJ (US); Ye Zhu, Singapore (SG)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/631,915

(22) PCT Filed: Jul. 19, 2018

(86) PCT No.: PCT/US2018/042797
§ 371 (c)(1),
(2) Date: Jan. 17, 2020

(87) PCT Pub. No.: WO2019/018592
PCT Pub. Date: Jan. 24, 2019

(65) Prior Publication Data
US 2020/0223852 A1    Jul. 16, 2020

Related U.S. Application Data

(60) Provisional application No. 62/534,908, filed on Jul. 20, 2017.

(51) Int. Cl.
*C07D 487/04*    (2006.01)
(52) U.S. Cl.
CPC .................. *C07D 487/04* (2013.01)
(58) Field of Classification Search
CPC .................................................. C07D 487/04
USPC ....................................................... 544/184
See application file for complete search history.

(56) References Cited

U.S. PATENT DOCUMENTS 8,383,812 B2    2/2013  Carter et al.

FOREIGN PATENT DOCUMENTS

WO    WO2008014360 A2    1/2008

OTHER PUBLICATIONS

Altamore, Timothy M., et al., "Concise Synthesis of Enantiomerically Pure(19S,29R)- and (19R,29S)-2S-Amino-3-(29-aminomethylcyclopropyl)propionic Acid: Two E-Diastereoisomers of 4,5-Methano-L-lysine", Australian J. Chem., 2013, vol. 66, pp. 1105-1111.
Norman, P., "A dual CCR2/CCR5 chemokine antagonist, BMS-813160?" Expert Opin. Ther. Patents, 2011, vol. 21, 12, pp. 1919-1924.

*Primary Examiner* — Douglas M Willis
(74) *Attorney, Agent, or Firm* — Elliott Korsen; Roy Issac

(57) ABSTRACT

The invention generally relates to an improved process for the preparation of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide,

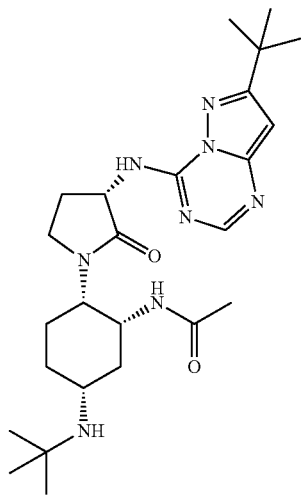

(I)

as well as novel intermediates employed in the process, which may be useful for the treatment of cancer.

1 Claim, No Drawings

PROCESS FOR THE PREPARATION OF N-((1R,2S,5R)-5-(*TERT*-BUTYLAMINO)-2-((S)-3-(7-*TERT*-BUTYLPYRAZOLO[1,5-A][1,3,5]TRIAZIN-4-YLAMINO)-2-OXO-PYRROLDIN-1-YL)CYCLOHEXYL)ACETAMIDE

CROSS-REFERENCE TO RELATED APPLICATIONS

This application is a national phase application under 35 U.S.C. § 371 of International Patent Application No. PCT/US2018/042797, filed Jul. 19, 2018, which claims priority to U.S. Provisional Application Ser. No. 62/534,908, filed Jul. 20, 2017, the contents of which are specifically incorporated fully herein by reference.

FIELD OF THE INVENTION

The invention generally relates to an improved processes for the preparation of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, a dual modulator of chemokine receptor activity.

BACKGROUND OF THE INVENTION

There is disclosed an improved processes for the preparation of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, of formula I.

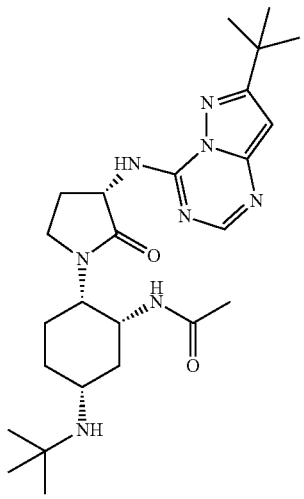
(I)

Compound I, crystalline forms of Compound I, compositions comprising Compound I, and an alternate process of preparing Compound I are disclosed in U.S. Pat. No. 8,383,812, which is assigned to the present assignee and is incorporated herein by reference in its entirety. Compound I may be useful in combination with certain anticancer agents for the treatment of various types of cancer.

SUMMARY OF THE INVENTION

In a first aspect, the invention provides a process for preparing Compound I of the formula:

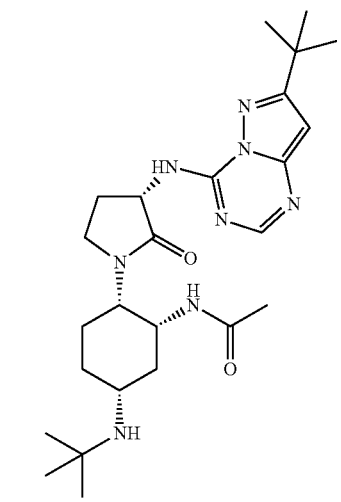
(I)

comprising the steps of
a) reacting Compound 1 of the formula

Compound 1

[chemical structure showing NHBoc cyclohexenone]

with Compound 2 of the general formula

Compound 2

$R_1$⌒NHAc where $R_1$ is a leaving group such as halogen, OAc, etc. and an acid, such as a mineral or organic acid such as MSA, CSA, ESA, or a Lewis acid, such as, LiX, $BF_3$-etherate, in a suitable solvent such as DCM, DCE, $CHCl_3$, $CCl_4$, diethyl ether, THF, methyl t-butyl ether or other ethereal solvents, to afford Compound 3 of the formula Compound 3

[chemical structure showing BocN, NAc cyclohexanone]

b) reacting Compound 3 in a reductive amination reaction with a primary or secondary amine ($HNR_2R_3$) wherein
$R_2$ and $R_3$ are hydrogen or $C_1$-$C_6$ alkyl;
mediated by a Lewis acid such as $Ti(Oi-Pr)_4$, followed by reaction with a suitable hydride donor, such as $NaBH_4$, or a combination of a catalyst such as Pt/Al or Pd/C and hydrogen gas, to afford Compound 4 of the formula Compound 4

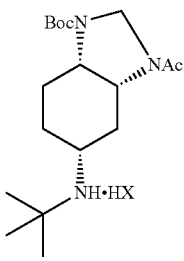

wherein Compound 4 can exist as the free base or the ammonium salt,
wherein X is an inorganic counter ion such as a halogen, sulfate, or an organic counter ion such as a tartrate, or citrate;
c) subsequently reacting the salt of Compound 4 with i-PrOH/H₂SO₄ or free basing first with NaOH and then with an appropriate acid/solvent mixture such as MSA/DCM in a ratio of 1:21.4 or H₂SO₄/IPA in a ratio of 1:588, to afford Compound 5 of the formula Compound 5

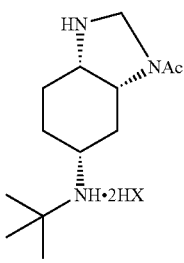

wherein Compound 5 can exist as the free base or the ammonium salt, wherein X is an inorganic counter ion such as a halogen, sulfate or an organic counter ion such as a tartrate, or citrate;
d) reacting Compound 5, or a salt thereof, in a reductive amination, in an appropriate solvent and using a hydride source such as triacetoxyborohydride, with Compound 6 of the formula Compound 6

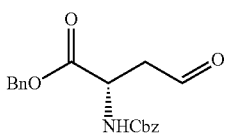

to afford Compound 7 of the formula,

Compound 7

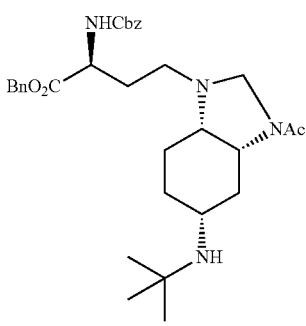

e) which is then reacted with an acid such as TFA, in the presence of NH₂OH, or its salt, and a suitable solvent to afford Compound 8 of the formula Compound 8

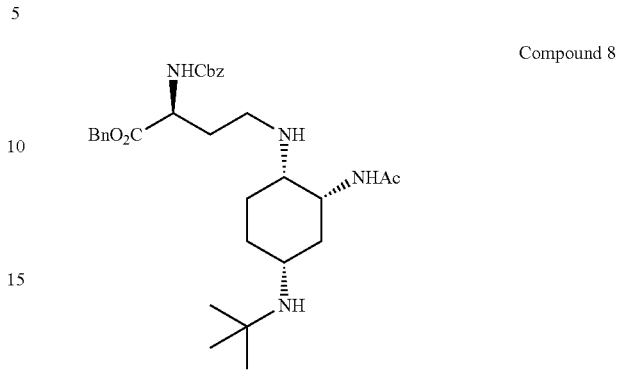

f) which is further reacted with an acid such as TFA, a base, and heated to 45-70° C. in an appropriate solvent, such as toluene, iso-propyl acetate, n-heptane, NMP, DMF, diethyl ether, THF, methyl t-butyl ether or other ethereal solvents or solvent mixtures to afford Compound 9 of the formula Compound 9

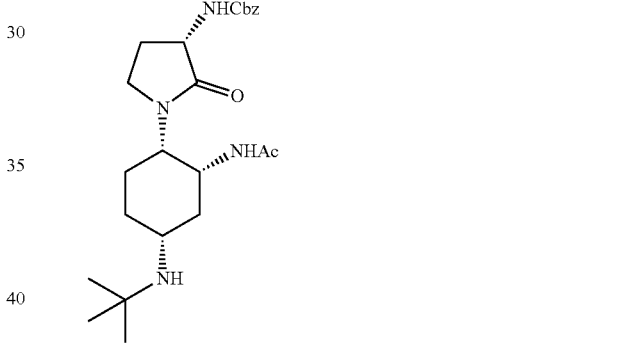

g) subsequently removing the protecting group by a suitable method, such as hydrogenation with Pd/C which can be isolated as the free base or a mono or bis salt formed by reacting with an acid such as HCl or HBr, where X is a halogen, to afford Compound 10 of the formula Compound 10

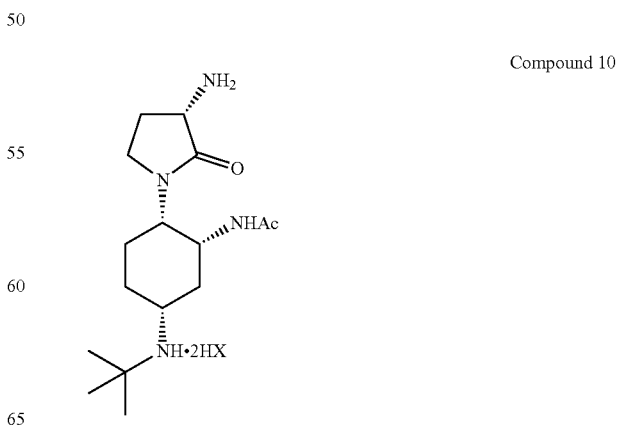

h) which is then reacted with Compound 11a of the formula

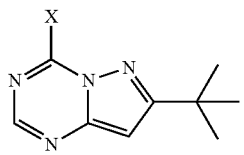
Compound 11a where X is a leaving group such as halogen, nitrogen or OR, where R is alkyl, aryl, a suitable phospho or sulfate ester, to afford Compound I, which is crystallized from a suitable solvent mixture such as 2-MeTHF/n-Heptane, or other ethereal/hydrocarbons.

In a second aspect, there is provided a process for the preparation of Compound 6 of the formula:

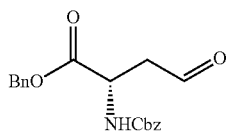
Compound 6 which comprises
a) reacting aspartic acid of the formula

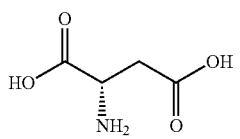
Compound 12 with a suitable reagent to protect the carboxylic acid group as an ester ($R_1$) and the amine group as an amide ($R_2$) such as a carbamate, sulfamide, phosphoramide, etc., to afford Compound 13 of the formula

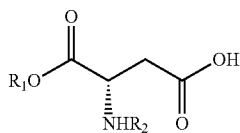
Compound 13 b) which is activated with a suitable reagent, such as DCC, Piv$_2$O, PiVCl, TCFH, or (COCl)$_2$ and then with a thiolating reagent such as dodecanethiol or other thiols ($R_3$) to afford Compound 14 of the formula

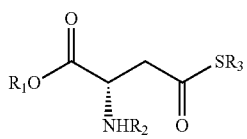
Compound 14 c) and, subsequently reacting Compound 14 with a suitable reducing agent such as Et$_3$SiH in the presence of a catalyst such as Pd/C or Pd/Al to afford Compound 6.

In a third aspect of the invention, there are provided novel intermediate compounds as shown in the table below;

| Compound No. | Structure |
|---|---|
| 3 | ![structure] |
| 4 | ![structure] |
| 4a | ![structure] |
| 5 | ![structure] |
| 5a | ![structure] |
| 7 | ![structure] |

| Compound No. | Structure |
|---|---|
| 8 | (structure: BnO₂C-CH(NHCbz)-CH₂-CH₂-NH-cyclohexyl(NHAc)(NH-tBu)) |
| 9 | (structure: pyrrolidinone with NHCbz, connected to cyclohexyl with NHAc and NH-tBu) |
| 10 | (structure: pyrrolidinone with NH₂, connected to cyclohexyl with NHAc and NH-tBu) |
| 10a | (structure: pyrrolidinone with NH₃⁺Br⁻, connected to cyclohexyl with NHAc and NH₂⁺Br⁻-tBu) |
| 14 | (structure: R₁O-C(O)-CH(NHR₂)-CH₂-C(O)-SR₃) |
| 14a | (structure: BnO-C(O)-CH(NH-C(O)-OBn)-CH₂-C(O)-S-(CH₂)₁₀-CH₃) | which are used in the process of the invention.

In one embodiment of the invention, there is disclosed the process wherein the leaving group in step a) of the first aspect is a halogen or OAc leaving group.

In one embodiment of the invention, there is disclosed the process wherein the acid in step a) of the first aspect is a mineral or organic acid.

In another embodiment of the invention, there is disclosed the process wherein the acid in step a) of the first aspect is MSA, CSA or ESA.

In another embodiment of the invention, there is disclosed the process wherein the acid in step a) of the first aspect is a Lewis acid.

In another embodiment of the invention, there is disclosed the process wherein the Lewis acid is LiX, where X is halogen, or $BF_3$-etherate.

In another embodiment of the invention, there is disclosed the process wherein the solvent in step a) of the first aspect is DCM, DCE, $CHCl_3$ or $CCl_4$ or a mixture thereof.

In another embodiment of the invention, there is disclosed the process wherein Compound 4 of the first aspect is the free base.

In another embodiment of the invention, there is disclosed the process wherein Compound 4 of the first aspect is the ammonium salt.

In another embodiment of the invention, there is disclosed the process wherein the acid/solvent mixture in step c) of the first aspect is MSA/DCM in a ratio of 1:21.4.

In another embodiment of the invention, there is disclosed the process wherein the acid in step e) of the first aspect is TFA and the solvent is toluene.

In another embodiment of the invention, there is disclosed the process wherein Compound 8 of the first aspect is reacted with an acid or a base.

In another embodiment of the invention, there is disclosed the process wherein Compound 8 is heated in a solvent/solvent mixture where the solvents are toluene, iso-propyl acetate, n-heptane, NMP, DMF, diethyl ether, THF, methyl t-butyl ether or other ethereal solvents.

In another embodiment of the invention, there is disclosed the process wherein the reductive amination in step b) of the first aspect uses Pd/C and MeOH and the reductive amination in step d) uses sodium triacetoxyborohydride.

In another embodiment of the invention, there is disclosed the process wherein the HBr salt of Compound 10 is formed in step g).

In another embodiment of the invention, there is disclosed the process wherein in step h) of the first aspect Compound 11 is activated with 1-methylimidazole and diphenyl phosphoryl chloride to afford Compound 11a.

In one embodiment of the invention, in step a) of the second aspect, $R_1$ is $C_1$-$C_6$ alkyl or benzyl; and $R_2$ is $C_1$-$C_6$ alkyl, —C(O)O $C_1$-$C_6$ alkyl, —C(O)O benzyl, —$SO_2$NH $C_1$-$C_6$ alkyl, —$SO_2$NH benzyl, —P(O)—N $C_1$-$C_6$ alkyl, —P(O)—N benzyl, —N—$C_1$-$C_6$ alkyl or N-benzyl.

In one embodiment of the invention, in step b) of the second aspect, $R_3$ is hydrogen, $C_1$-$C_{12}$ alkyl or benzyl.

In another embodiment of the invention, there is disclosed the process wherein the activating reagent in step b) of the second aspect is DCC, $Piv_2O$, PivCl, or $(COCl)_2$ In another embodiment of the invention, there is disclosed the process wherein the activating reagent in step b) of the second aspect is dodecanethiol or other thiols ($R_3$)

In another embodiment of the invention, there is disclosed the process wherein the reducing agent in step c) of the second aspect is Pd/C and the reducing agent is $Et_3SiH$.

Another aspect of the invention provides Compound I prepared by the processes described herein.

A final aspect of the invention provides a method for treating cancer, comprising administering to a mammalian species, preferably a human, in need thereof, a therapeutically effective amount of Compound I in combination with another anti-cancer agent, preferably nivolumab, wherein Compound I is prepared utilizing the novel process steps of the invention.

The processes of the invention have several important advantages over prior syntheses of Compound I. In particular, due to the short sequence of chemical steps, high yields and process improvement, the throughput, cycle-time and overall yield have been dramatically improved. Additionally, the process consistently provides Compound I in high quality for use as a pharmaceutical API.

DETAILED DESCRIPTION OF THE INVENTION

Examples

The invention will now be further described by the following working example(s), which are preferred embodiments of the invention. All temperatures are in degrees Celsius (° C.) unless otherwise indicated. These examples are illustrative rather than limiting and it is to be understood that there may be other embodiments that fall within the spirit and scope of the invention as defined by the claims appended hereto.

For ease of reference, the following abbreviations may be used herein.

| Abbreviations | Name |
|---|---|
| $CH_3CN$, MeCN | acetonitrile |
| aq. | aqueous |
| Bn | benzyl |
| Boc | t-butyl carbamate |
| $Boc_2O$ | di-t-butyl dicarbonate |
| Bu | butyl |
| Cbz | benzyl carbamate |
| conc. | concentrated |
| DCC | dicyclohexylcarbodiimide |
| DCE | dichloroethane |
| DCM | dichloromethane |
| DEA | diethanolamine |
| DMAP | 4-N,N-dimethylaminopyridine |
| DMF | dimethyl formamide |
| DMSO | dimethyl sulfoxide |
| eq. | equivalents |
| Et | ethyl |
| EtOAc | ethyl acetate |
| EtOH | ethanol |
| $Et_2O$ | diethyl ether |

-continued

| Abbreviations | Name |
|---|---|
| $Et_3N$ | triethylamine |
| $Et_3SiH$ | triethylsilane |
| h | hour(s) |
| HPLC | high pressure liquid chromatography |
| $H_2SO_4$ | sulfuric acid |
| IPAc | isopropyl acetate |
| i-PrOH | isopropanol |
| Kf, kf | Karl Fischer |
| kLa | mass-transfer coefficient |
| LAH | lithium aluminum hydride |
| Me | methyl |
| MeOH | methanol |
| MSA | methanesulfonic acid |
| MTBE | methyl t-butyl ether |
| $NH_2OH$ | hydroxylamine |
| NMI | 1-Methylimidazole |
| NMR | nuclear magnetic resonance |
| Pt/Al | platinum on alumina |
| $Pd/Al_2O_3$ | palladium on alumina |
| Pd/C | palladium on carbon |
| Ph | phenyl |
| RAP | Relative area percent |
| rt/RT | room temperature |
| sat. | saturated |
| STAB | sodium triacetoxyborohydride |
| t-Bu | tertiary butyl |
| t-BuOH | tertiary butanol |
| TCFH | tetramethylchloroformamidinium hexafluorophosphate |
| TFA | trifluoroacetic acid |
| THF | tetrahydrofuran |
| $Ti(OPr)_4$ | titanium(IV) isopropoxide |
| Z-ASP-OBZL | N-Cbz-L-aspartic acid β-benzyl ester |

Example 1

Preparation of Compound 3

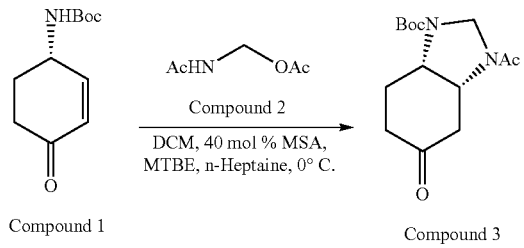

25 g Compound 1 scale, equivalencies calculated based on Compound 1

Step 1: Reaction

A 250 ml Chemglass reactor was charged with Compound 1 (25.0 g), Compound 2 (24.8 g, 1.6 equiv.) and DCM (47.4 mL). The reaction mixture was stirred until all solids dissolved and then cooled to 0° C. To the reaction mixture was added a solution of MSA, (3.07 ml, 0.40 equiv.) in DCM (11.8 mL) dropwise at a rate such that the internal temperature of the reaction mixture did not increase above 2° C. (~30 min). The reaction stream was then aged at ~0° C. for 21-24 h.

Step 2: Work-Up

The reaction was quenched with the addition of aq. NaOAc (0.5 M, 125 ml) and followed by an additional charge of DCM (175 mL). The biphasic mixture was mixed and the phases were split. The product rich organic phase was washed with water (150 mL) and then with 10% (w/w) $Na_2HPO_{4(aq)}$ (~150 mL, until the pH of the aqueous layer >7). The layers were allowed to settle and then separated.

Step 3: Drying

The product rich organic stream was distilled to a minimum volume and then followed by constant volume distillation by the portion wise addition of MTBE (~100 mL portions 80° C. jacket temperature) until the molar ratio contents of distillate were ~200:1 MTBE/DCM and residual water was measured <0.1 wt %. The product stream was then concentrated to a final volume of ~130 mL (~31 wt % Compound 3 in MTBE).

Step 4: Crystallization

The product rich stream was cooled to 50° C. and n-Heptane (50.5 mL) was slowly added over a 10 min period (~25 wt % solution of Compound 3 in ~35% n-Heptane/MTBE (vol/vol)). Solid Compound 3 (0.63 g, equivalent to ~2 wt % of Compound 3 present in the process stream) was then added and the mixture was aged at ~50° C. for ~30 min. The subsequent slurry was cooled to ~22° C. over a 3 h period, aged at 22° C. for 3 h, further cooled to ~0° C. over a 3 h period and aged at this temperature until <6 wt % of the Compound 3 mass initially present remained in the supernatant.

Step 5: Isolation

The slurry was filter slurry at 0° C. and washed twice with 50:50 n-Heptane/MTBE (vol/vol) (~75-100 mL).

Step 6: Drying

Isolated Compound 3 was dried at room temperature under full vacuum. 27.70 g of Compound 3 was isolated (82.9% yield, >99% LCAP at λ205 nm, 100% potency) of as a white solid.

HPLC Analysis:

Compound 3: 98.9 AP (8.46 min);

Gradient=Start % B=0

Final % B=100

Gradient Time=10 min

Flow Rate=1 ml/min

Wavelength1=205

Wavelength2=220

Solvent A=0.05% TFA in MeOH:Water (20:80)

Solvent B=0.05% TFA in MeOH:$CH_3CN$ (20:80)

Column: Phenomenex Luna C18(2) 3 um 4.6×150 mm

NMR data is presented as a mixture of rotamers:

$^1H$ NMR (400 MHz, CHLOROFORM-d) δ 1.45 (s, 38H), 1.94-2.08 (m, 13H), 2.08-2.47 (m, 17H), 2.48-2.61 (m, 1H), 2.62-2.83 (m, 8H), 4.25-4.34 (m, 3H), 4.36 (br. s., 1H), 4.42-4.56 (m, 2H), 4.64 (d, J=6.82 Hz, 3H), 4.70-4.81 (m, 3H), 4.93 (br. s., 3H), 5.19 (br. s., 1H) ppm.

$^{13}C$ NMR (101 MHz, CHLOROFORM-d) δ 21.30 (s, 1C), 22.57 (s, 1C), 28.21 (s, 1C), 34.76 (s, 1C), 40.86 (s, 1C), 42.88 (s, 1C), 53.45 (s, 1C), 54.11 (s, 1C), 54.81 (s, 1C), 55.40 (s, 1C), 60.27 (s, 1C), 61.48 (s, 1C), 81.10 (s, 1C), 152.65 (s, 1C), 153.02 (s, 1C), 167.54 (s, 1C), 208.30 (s, 1C), 209.51 (s, 1C) ppm.

Example 2

Preparation of Compound 4a

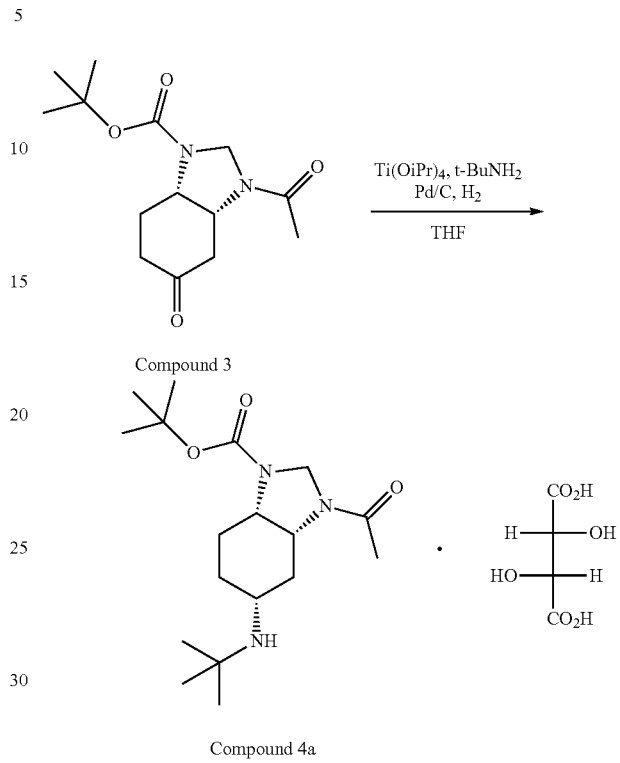

All the equivalencies were calculated based on Compound 3 (300.0 g).

Step 1: Imine Formation

Into a 4 liter bottle (Reactor A) was added (3aR,7aS)-tert-butyl 3-acetyl-5-oxooctahydro-1H-benzo[d]imidazole-1-carboxylate (Compound 3, 1.0 equiv, 1.06 mol), THF (5 L/kg), titanium tetra(isopropoxide) (1.7 equiv, 1.81 mol) and 2-methyl-2-propanamine, (1.5 equiv, 1.59 mol). The resulting mixture was aged for 4-16 h at 25° C.

Step 2: Reductive Amination

Into a 5 L Buchi reactor (Reactor B) was added Pd/C (54% wet; 5 wt %, 13.5 mmol) and MeOH (0.67 L/kg). The mixture was filtered and rinsed with THF (0.5 L/kg×3) then transferred back to Reactor B. The imine mixture from Reactor A was then added to Reactor B. Reactor A was rinsed with THF (0.67 L/kg) and the rinse was added to Reactor B. Reactor B was flushed with nitrogen three times, followed by hydrogen two times. Reactor B was then pressurized with hydrogen to 30 psi and stirred at 600 rpm for 2 h.

Step 3: Reaction Workup

The reaction mixture was filtered through a 0.5 micron Cuno filter. Reactor B was then rinsed with THF (0.83 L/kg×2). The combined filtrate and rinse was added to a 10 L Chemglass reactor (Reactor C) followed by 2-propaneamine (2.0 equiv, 2.12 mol), and 5 N NaOH (0.37 equiv, 375 mmol). The mixture was stirred for 16 h at room temperature, and then filtered. The reactor and cake were washed with THF (4 L/kg×2), then the cake was washed with additional THF (3.3 L/kg). The cloudy filtrate was filtered again, then added to a 10 L Chemglass reactor (Reactor D) followed by the rinses.

Step 4: Crystallization

The mixture in Reactor D was concentrated under reduced pressure to 2.7 L/kg, then the solvent was swapped to acetone through a put and take distillation. During this operation, acetone (5.4 L/kg) was used and 5.4 L/kg solvent was removed from Reactor D. To the mixture was added acetone (10.6 L/kg), then a solution of L-tartaric acid (0.93 equiv, 988 mmol) in MeOH (1 L/kg), and then additional acetone (5.7 L/kg) at 45° C. The resulting mixture was cooled to 25° C. over 2 h and aged for 16 h.

Step 5: Isolation:

The slurry in Reactor D was filtered. The reactor was rinsed with acetone (2.7 L/kg). The cake was then washed with this reactor rinse, followed by acetone (2.3 L/kg). The product was dried under vacuum at 35° C. for 5 h. The product, Compound 4a, (3aR,5R,7aS)-tert-butyl 3-acetyl-5-(tert-butylamino)octahydro-1H-benzo[d]imidazole-1-carboxylate 2,3-dihydroxysuccinate was isolated as a white solid powder. 462 g, 89% yield.

Alternative Procedures

Step 2: Alternative Reductive Amination

Reactor B was evacuated with nitrogen. The reaction solution from Reactor A was transferred to Reactor B. 5% Platinum on Alumina (Pt/Al, 0.10 kg, 0.10 kg/kg) was charged into Reactor B, followed by a rinse with tetrahydrofuran from Reactor A to Reactor B (1.0 L, 0.89 kg, 1.0 L/kg). Reactor B was purged twice with nitrogen at 20-30° C. The mixture was stirred at 25° C., 0.45-0.55 MPa for 16 h. Reactor B and then vented and purged with nitrogen. The mixture was filtered into Reactor A and tetrahydrofuran (1.0 L, 0.89 kg, 1.0 L/kg) was used as a rinse.

Step 3: Alternative Reaction Work-Up

Water (7.5 L, 7.5 kg, 7.5 L/kg) and ammonium citrate tribasic (4.39 kg, 5.1 equiv) were charged to Reactor C. Reaction stream from Reactor A was transferred to Reactor C at a rate such that the temperature did not exceed 30° C. The mixture in Reactor C was heated to 40-50° C. and aged for 1 h. The mixture in Reactor C was cooled to 15-25° C. and stirred for 0.5 h. Agitation was stopped and phases were allowed to settle for 1 h at 15-25° C. (target 20° C.). The phases were separated and the lower aqueous layer from Reactor C was sent to waste.

The batch was concentrated until 2-3 L/kg remained with respect to (3aR,7aS)-tert-butyl 3-acetyl-5-oxooctahydro-1H-benzo[d]imidazole-1-carboxylate (Compound 3). Methyl tert-butyl ether was charged (5.0 L, 3.7 kg, 5.0 L/kg) at NMT 50° C. into Reactor C. The batch was again concentrated until 2-3 L/kg remaining with respect to Compound 3. Methyl-tert-butyl ether (10.0 L, 7.4 kg, 10.0 L/kg) was then charged into Reactor C.

Reactor A (prerinsed) was charged with water (0.94 L, 0.94 kg, 0.94 L/kg) and sodium chloride (0.10 kg, 0.10 kg/kg). Temperature of the mass in Reactor C was adjusted to 15-25° C. The sodium chloride solution from Reactor A was added to the mass in Reactor C and agitated for 0.5 h. Agitation was stopped and phases allowed to settle for 1 h at 15-25° C. target 20° C. Phases were then separated and the lower aqueous layer from Reactor C was sent to waste.

The reaction stream from Reactor C was filtered into a clean and nitrogen-filled Reactor D. Added Methanol (5.0 L, 3.96 kg, 5.0 L/kg) into Reactor C, then transferred to Reactor D. The batch in reactor D was concentrated until 2-3 L/kg remained with respect to Compound 3.

Step 4: Alternative Crystallization

Charged Methanol to Reactor D (4.0 L, 3.16 kg, 4.0 L/kg) through an in-line filter at NMT 50° C. The amount of Compound 4 in solution was quantified. Added Methanol (2.0 L, 1.58 kg, 2.0 L/kg) and L-(+)-Tartaric Acid (1.15 equiv relative to compound 4 in solution) into Reactor C at 10-30° C. The solution of L-(+)-Tartaric Acid was then transferred to Reactor D through an in-line filter at 20-30° C. and the solution in Reactor D was heated to 48-53° C. MTBE (18.0 L, 13.3 kg, 18.0 L/kg) was then charged to Reactor D at 48-53° C. at a rate such that the temperature stays above 48° C. The reaction mixture was aged at 48-53° C. until solid precipitation is observed, then cooled to 20-25° C. at a rate of 5-10° C./h, and aged for 4 h.

Step 5: Alternative Isolation

The solids were then filtered. Methyl tert-Butyl Ether (2.0 L, 1.48 kg, 2.0 L/kg) was charged to Reactor D through an in-line filter and used to rinse the product cake. The cake was dried at a jacket set point of 45-50° C., under reduced pressure with a nitrogen sweep for NLT 10 h.

HPLC Analysis:

Compound 4a: 99.6 AP (6.8 min)
Column: YMC ProC18 Sum 50×4.6 mm
Solvent A: 0.05% TFA in $CH_3CN$:Water (5:95)
Solvent B: 0.05% TFA in $CH_3CN$
Gradient: % B: 0 Min. 0%; 8 Min. 25%; 0 Min. 100%; Stop Time: 12 min
Flow Rate: 1.0 ml/min
Wavelength: 205 nm $^1$H NMR (400 MHz, Methanol-$d_4$) δ 4.98 (d, J=8.6 Hz, 1H), 4.92 (d, J=7.1 Hz, 1H), 4.58 (d, J=8.8 Hz, 1H), 4.45 (dt, J=10.9, 5.8 Hz, 1H), 4.36-4.30 (m, 4.4H), 3.85-3.82 (m, 1H), 3.76-3.73 (m, 1H), 3.42-3.35 (m, 2H), 3.27 (ddd, J=4.8, 3.3, 1.5 Hz, 4.4H), 2.93 (d, J=14.4 Hz, 1H), 2.81 (d, J=15.9 Hz, 1H), 2.39-2.33 (m, 1H), 2.27-2.21 (m, 1H), 2.09 (s, 3H), 2.02 (s, 3H), 1.90-1.83 (m, 2H), 1.82-1.71 (m, 2H), 1.65-1.51 (m, 3H), 1.46 (s, 9H), 1.45 (s, 9H), 1.39 (s, 9H), 1.38 (s, 9H), 1.32-1.21 (m, 1H).

$^{13}$C NMR (100 MHz, Methanol-$d_4$) δ 177.3, 170.2, 170.1, 156.2, 155.9, 82.6, 82.4, 74.4, 62.3, 61.4, 59.5, 59.4, 57.9, 56.5, 55.6, 55.4, 51.6, 51.3, 50.0, 33.4, 31.8, 30.9, 28.8, 26.7, 26.7, 26.6, 26.5, 24.9, 22.1, 21.2.

Example 3

Preparation of Compound 9

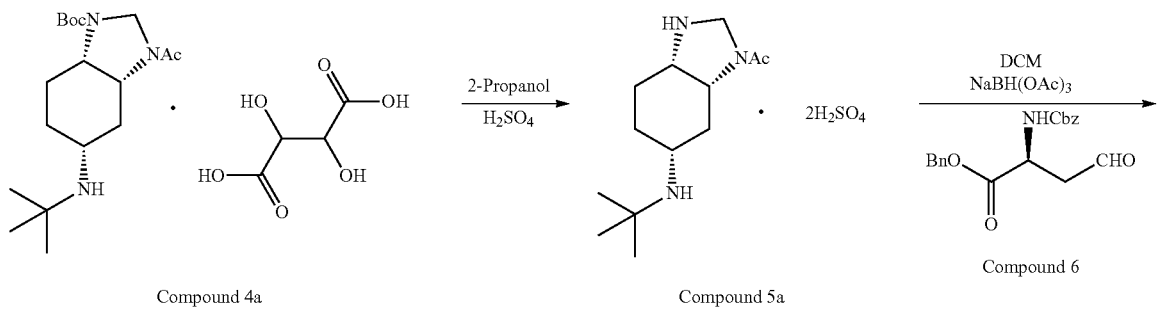

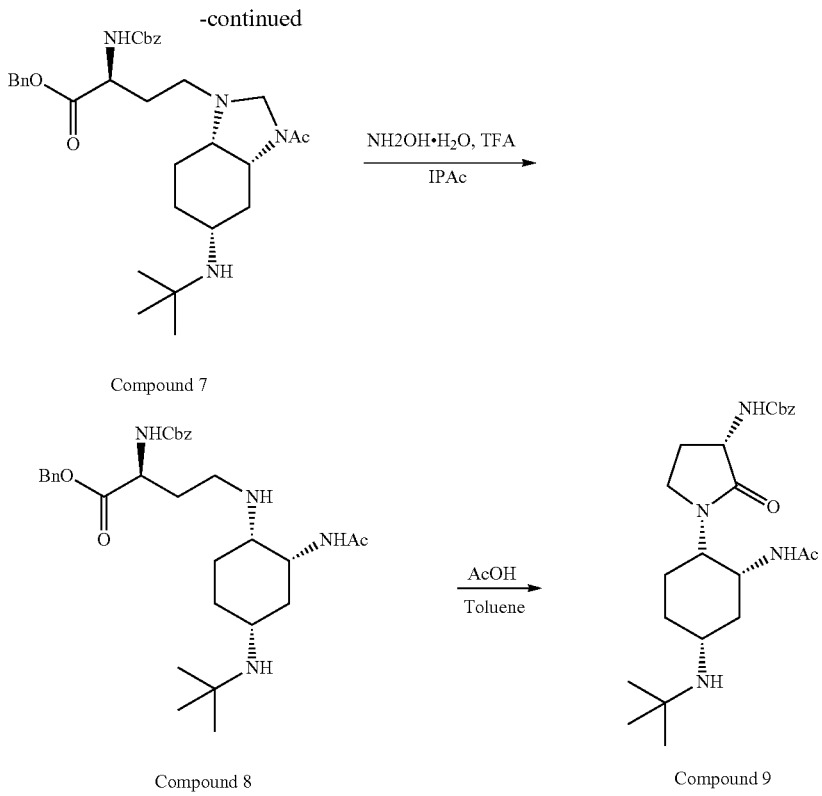

benzyl ((S)-1-((1S,2R,4R)-2-acetamido-4-(tert-butylamino)cyclohexyl)-2-oxopyrrolidin-3-yl)carbamate Step 1: Boc-Deprotection Compound 4a 50 g, (102.13 mmol) and 2-propanol (4 mL/gram limiting reagent) are mixed, and heated to 58° C. Concentrated sulfuric acid (0.63 g/gram of limiting reagent or 3 equiv) was charged to the reaction mixture over ~1 h and aged at 58° C. for 4 h total. The batch was cooled to 40° C., and the solids were then filtered. The cake was washed with 2-propanol (2 ml/gram limiting reagent), and dried at 60° C. for 12 h to give compound 5a.

$^1$H NMR (500 MHz, DMSO-d6) δ 10.53-8.96 (m, 9H), 8.38-8.03 (m, 5H), 7.98 (br d, J=7.0 Hz, 1H), 7.86 (br d, J=2.7 Hz, 1H), 4.86 (d, J=7.9 Hz, 1H), 4.74 (d, J=7.9 Hz, 1H), 4.68-4.52 (m, 4H), 4.46 (dt, J=11.3, 6.0 Hz, 1H), 3.90 (br s, 2H), 3.78 (br d, J=4.6 Hz, 1H), 3.40 (br s, 3H), 2.41-2.21 (m, 3H), 2.21-1.95 (m, 13H), 1.93-1.77 (m, 5H), 1.61 (q, J=12.2 Hz, 2H), 1.52-1.40 (m, 1H), 1.33 (br d, J=12.2 Hz, 24H), 1.04 (d, J=6.1 Hz, 1H).

Steps 2 through 5: All the equivalencies were calculated based on Compound 5a.

Step 2: Reductive Amination

In a 2 L reactor containing a mixture of Compound 5a (58.01 g, 1.0 equiv., 133.8 mmol), Compound 6 (47.95 g, 1.05 equiv., 140.5 mmol) and DIPEA (69.02 g, 4.0 equiv., 535.2 mmol) in methylene chloride (DCM, 870 mL, 15 L/kg) was added sodium triacetoxyborohydride (32.16 g, 1.13 equiv., 151.7 mmol) and the resulting reaction mass was stirred at room temperature. Upon reaction completion as per HPLC analysis, water (580 mL, 10 L/kg) was added slowly and the resulting biphasic liquid mixture was stirred for 12 hours whereupon the agitation was stopped to allow the phase separation. The lower organic layer was concentrated down to 290 mL residual volume under reduced pressure and isopropyl acetate (IPAc, 580 mL, 10 L/kg) was charged in the reactor. The resulting homogeneous mixture was concentrated again to a residual volume of 290 mL under a reduced pressure of 200 mbar. Upon a second addition of IPAc (290 mL, 5 L/kg) the mixture was concentrated a third time to a residual volume of 290 mL and a third IPAc charge (232 mL, 4 L/kg) was performed providing a rich solution of Compound 7 in IPAc (9 L/kg) ready for processing in the next step.

Step 3: Cleavage of the Methylene Tether

To the aforementioned solution of Compound 7 cooled to 10° C., was added a solution of 50 wt % aqueous hydroxylamine (11.36 g, 1.30 equiv., 172.0 mmol) followed by TFA (51.84 g, 3.4 equiv., 454.6 mmol). The resulting mixture was heated at 56-57° C. for 4.5 hours. Upon completion of the reaction as per HPLC analysis, the heterogeneous mixture was cooled to 0° C. and 290 mL of 2 N aqueous NaOH (580 mmol, 4.35 eq) was slowly added between 5 and 10° C. The biphasic mixture was stirred for 1 hour at 5-10° C. before stopping agitation to allow the phase split. The upper organic layer was treated with 220 mL of 17 wt % aqueous K$_3$PO$_4$ at 5° C. for 1 hour with agitation and for 30 minutes without agitation to allow the phases to split. The upper organic layer was washed at 10° C. with 232 mL of 14 wt % aqueous NaCl (4 L/kg) for 30 min with agitation and 30 minutes without agitation to allow the phase separation. The upper organic layer was concentrated to a residual volume of 290 mL (5 L/kg) under a reduced pressure of 100 mbar whereupon toluene (464 mL, 8 L/kg) was added and the resulting mixture was concentrated a second time down to 290 mL at 100 mbar and a jacket temperature<70° C. A second toluene addition (464 mL, 8 L/kg) followed by a third concentration to 5 L/kg residual was performed under the same temperature and pressure conditions whereupon the distillation residue was diluted with more toluene (232 mL, 4 L/kg) to give a dry toluene solution of Compound 8 ready for processing in the next step.

Step 4: Annulation to Form Compound 9

The Compound 8 rich toluene solution was treated with acetic acid (14.15 g, 1.75 equiv. 235.6 mmol) and the resulting mixture was heated under agitation at 57° C. for 5 hours at which point the reaction was complete as indicated by HPLC analysis. The reaction mixture was cooled to 25° C. whereupon water (523 mL, 9 L/kg) was added and the biphasic mixture was kept for 1 hour with agitation and 1 hour without agitation before transferring the Compound 9 rich aqueous layer into a new reactor. The aqueous layer was mixed with IPAc (1.16 L, 20 L/kg) at 25-30° C. and 40 wt % aqueous $K_3PO_4$ (149 mL, 3 equiv.) was added and the biphasic mixture was stirred for 45 min before allowing the phase split and transfer of Compound 9 from the aqueous layer to the organic layer. The organic layer was washed with water (175 mL, 3 L/kg) at 25-30° C. with agitation before discarding the aqueous wash upon phase split. The organic layer was concentrated down to 525 mL (9 L/kg) residual under a pressure of 300 mbar with the jacket temperature<75° C. whereupon IPAc (290 mL) was charged and distilled to 525 mL performed again to dry the mixture to no more than 500 ppm of residual water.

Step 5: Crystallization and Isolation

The distillation residue was diluted with IPAc (60 mL, 1 L/kg) and the temperature was adjusted to 60° C. and 1 wt % of Compound 9 seeds (580 mg) were added to promote crystallization. The resulting slurry was aged for 2 hours at 55-60° C. whereupon further crystallization was promoted by the slow addition of n-Heptane (270 mL, 4.65 L/kg). The slurry was cooled to 20° C. in at least 2 hours, agitated for several hours before the solids were collected by filtration, washed once with IPAc/n-heptane 35/65 v/v (4.5 L/kg) and once with n-heptane (7.5 L/kg). The filter cake was dried under vacuum at 60° C. to provide Compound 9 as a white solid (45.87 g, 76.2 yield).

HPLC Analysis:

BnOH: 0.1 AP (5.33 min); Compound 9, benzyl ((S)-1-((1S,2R,4R)-2-acetamido-4-(tert-butylamino)cyclohexyl)-2-oxopyrrolidin-3-yl)carbamate: 99.5 AP (6.91 min); unidentified impurity I: 0.3 AP (7.63 min); unidentified impurity II; 0.2 AP (9.86 min).

Column: YMC ProC18 5um 4.6×50 mm
Solvent A: 0.05% TFA in $CH_3CN$:Water (5:95)
Solvent B: 0.05% TFA in $CH_3CN$
Gradient: % B: 0 Min. 0%; 8 Min. 25%; 15 Min. 100%
Flow Rate: 1.0 mL/min
Wavelength: 205 nm $^1$H NMR (400 MHz, $CDCl_3$) δ 9.35 (br s, 1H), 7.37-7.26 (m, 5H), 6.00 (br d, J=7.1 Hz, 1H), 5.10 (s, 2H), 4.56 (br s, 1H), 4.31 (q, J=7.4 Hz, 1H), 3.93 (br d, J=11.6 Hz, 1H), 3.36 (br t, J=6.6 Hz, 2H), 3.15 (br t, J=3.0 Hz, 1H), 2.47-2.31 (m, 1H), 2.12-1.99 (m, 1H), 1.91 (s, 3H), 1.87-1.57 (m, 6H), 1.12 (s, 9H) ppm.

$^{13}$C NMR (101 MHz, $CDCl_3$) δ 172.22, 169.57, 156.60, 136.65, 128.36, 127.94, 127.83, 83.64, 66.60, 53.66, 52.99, 51.61, 47.81, 45.89, 42.91, 34.32, 33.59, 29.66, 28.32, 23.81, 19.86 ppm.

Example 4

Preparation of Compound 10a

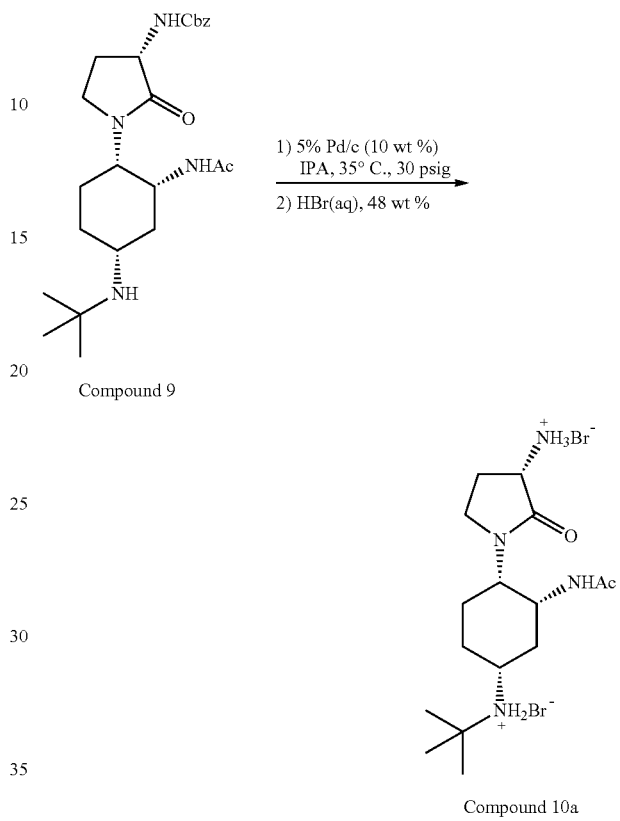

All the equivalencies were calculated based on benzyl ((S)-1-((1S,2R,4R)-2-acetamido-4-(tert-butylamino)cyclohexyl)-2-oxopyrrolidin-3-yl)carbamate (Compound 9; 10.0 g).

Step 1: Hydrogenation Reaction

A 300 mL Parr bomb reactor was charged with 7.1 kg/kg (9 L/kg) i-PrOH, benzyl ((S)-1-((1S,2R,4R)-2-acetamido-4-(tert-butylamino)cyclohexyl)-2-oxopyrrolidin-3-yl)carbamate (Compound 9; 10.0 g), and 0.05 kg/kg (5 wt %) of 5% Pd/C 50% water catalyst. The vessel was then sealed and made inert. The sequence of pressurizing to 30 psig with $N_2$, then venting down to 8 psig was repeated three times. The atmosphere was changed to hydrogen by performing the sequence of pressurizing to 30 psig with $H_2$, then venting down to 8 psig three times. The pressure was set to 30 psig, and set to keep at constant pressure throughout the course of the reaction. The jacket was set to heat the reaction mixture to 35° C. The agitation was set such that the kLa>0.02 $s^{-1}$. The mixture was stirred at 35° C. and 30 psig for 3-5 hours. The vessel was vented, then flushed with $N_2$ by pressurizing to 30 psig and venting the vessel down to 8 psig three times. HPLC analysis showed <0.30 RAP starting material.

Step 2: Reaction Workup

The reaction mixture was filtered through a 0.5 μm filter, then a 0.2 μm Cuno cartridge filter and rinsed with 2-propanol (2 L/kg) into a clean reactor.

Step 3: Crystallization

A vessel was charged with 7.9 kg/kg (10 L/kg) of i-PrOH, heated to 50° C. under an inert atmosphere followed by HBr 0.95 kg/kg (2.5 mol/mol; 48 wt %, aqueous). 1.88 kg/kg (18 wt % of total process stream) containing free base compound 10 was added to the HBr solution and aged for 1-3 h at 45-50° C. 8.54 kg/kg (82 wt % of total process stream) of free base process stream was charged over a 1 h period, the solution was aged at 50° C. for 1 h and then cooled to 20° C. over the course of 1 h. The slurry was filtered and the reactor was rinsed with 3 L/kg of i-PrOH. The cake was then washed with the reactor rinse. The cake was washed twice with 2-propanol (3 L/kg). The wet cake was dried in a vacuum oven at 70° C. under vacuum for 24 h. The product (S)-1-((1S,2R,4R)-2-acetamido-4-(tert-butylammonio)cyclohexyl)-2-oxopyrrolidin-3-aminium bromide (Compound 10a) was isolated as a white solid powder (86% yield).

HPLC Analysis:
Benzyl alcohol: <0.20 AP (3.7 min); N-((1R,2S,5R)-2-((S)-3-amino-2-oxopyrrolidin-1-yl)-5-(tert-butylamino)cyclohexyl)acetamide (Compound 9): >99.60 AP (4.7 min); benzyl ((S)-1-((1S,2R,4R)-2-acetamido-4-(tert-butylamino)cyclohexyl)-2-oxopyrrolidin-3-yl)carbamate (Compound 8): <0.20 AP (13.3 min).
Column: Waters XBridge Phenyl, 3.5 μm, 4.6×150 mm
Solvent A: Water:MeCN:MeOH (90:8:2+0.05% NH$_4$OH)
Solvent B: MeCN:MeOH (80:20+0.05% NH$_4$OH)
Gradient: % B: 0 min 22%; 20 min 55%; 25 min 90%; 30 min 22%; 35 min 22%; Stop time=35 min
Flow rate: 1 mL/min
Wavelength: 220 and 205 nm
Injection volume: 10 μL
Column temperature: ambient $^1$H NMR (400 MHz, DMSO-d$_6$) δ 8.39 (br s, 5H), 7.80 (d, J=8.6 Hz, 1H), 4.23-4.06 (m, 2H), 3.95 (t, J=9.2 Hz, 1H), 3.87 (br t, J=8.6 Hz, 1H), 3.67-3.51 (m, 2H), 2.45-2.32 (m, 1H), 2.15 (dq, J=12.4, 9.0 Hz, 1H), 2.02-1.67 (m, 9H), 1.45-1.28 (m, 9H); $^3$C NMR (101 MHz, DMSO-d$_6$) δ 170.5, 168.9, 57.8, 51.0, 49.8, 47.5, 47.2, 45.2, 32.7, 26.5, 26.0, 24.8, 23.6, 22.7

Example 5

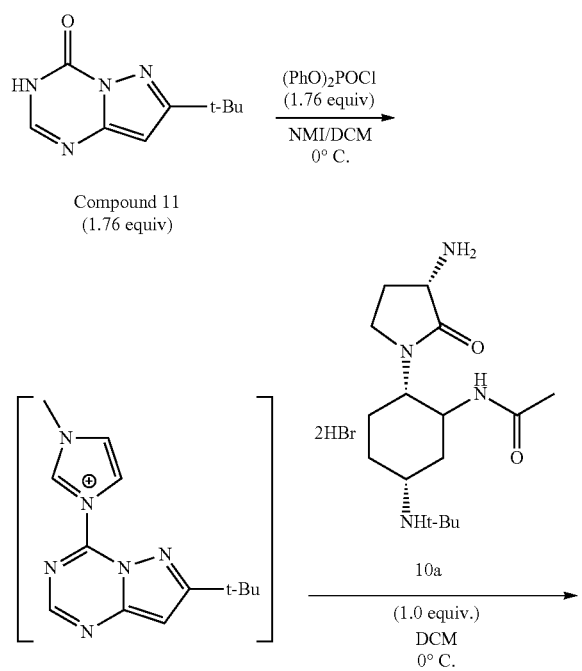

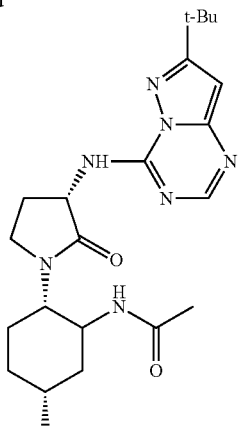

Compound I

Example 5

Preparation of Compound I

Step 1: Activation of Compound 11
Compound 11 (7.16 g, 1.76 equiv), 1-methylimidazole (66 ml,) and dichloromethane (DCM, 44 ml) were charged into a jacketed-reactor equipped with overhead stirring. The jacket temperature was set to 0° C. Diphenyl phosphoryl chloride (1.76 equiv., 7.75 mL) was added dropwise at a rate such that the batch temperature was maintained <5° C. The reaction mixture was aged for ~ 20 h at 0° C. and sampled (25 uL in 10 ml anhydrous MeOH) for reaction completion.

Step 2: Coupling Reaction
The process stream in step 1 was diluted with DCM (25 ml), Compound 10a (1.0 equiv, 10.0 g) was added to the reaction mixture at 0° C., followed by a second DCM charge (25 ml) and the process stream aged for 5-20 h.

Step 3: Work-Up
The reaction mixture was diluted with DCM (60 mL) and then quenched by the slow addition of a solution of citric acid monohydrate (57.4 g) in water (77.6 ml) to the process stream, followed by the addition of saturated NaCl(aq) solution (26 wt % in water, 82.5 ml). After mixing, the phases were separated, the product rich DCM layer was washed with a solution of NaOH (10 equiv) dissolved in water (150 ml); the phases were mixed, split, and the product rich DCM layer was extracted with water HCl (5 equiv in 150 ml water). The phases were separated; the organic layer discarded, and the product rich aqueous phase was treated with DCM (150 ml) and NaOH (6 equiv), the layers mixed and then separated. The product rich DCM layer was washed with water (50 ml).

Step 4: Distillation-Polish Filtration
The wet product rich DCM process stream was polish filtered into a reactor, concentrated by vacuum distillation (300 mbar, jacket 30° C.) to 5 L/kg, then constant volume solvent swap to 2-methyl THF (9 L/kg), maintaining volume at 5 L/kg. When distillation was complete, 7 L/kg 2-methyl THF was added. Distillation and solvent swap were complete when KF (<0.1 wt %) and residual DCM level (<3 wt % DCM) met specifications.

Step 5: Crystallization-Isolation
The batch was heated to 60° C. until the solids dissolved, and the reaction was cooled to 40° C. The reaction was charged with 1 wt % compound I and aged for 2 h. The batch was cooled to 20° C. over a 2 h period, and n-heptane (23 L/kg) was charged over a 2 h period. The slurry was aged overnight, filtered, and the reactor and cake were washed with 5 L/kg of 40:60 (wt/wt) 2-methyl THF to n-heptane. The cake was washed twice with 5 L/kg n-heptane and then dried under vacuum at 60° C. The final product, Compound I, was isolated as a white solid (80% yield)

Compound I

The numbering system shown above is for convenience only and may not be consistent with IUPAC nomenclature.

$^1$H NMR Assignments of Compound I

| Assignment | Chemical Shift$^{a,b}$ | Multiplicity$^c$, JHz | Number of Protons |
|---|---|---|---|
| 2 | 4.86 | t, 8.9 | 1 |
| 3 | 2.36 | m | 1 |
|   | 2.05 | m | 1 |
| 4 | 3.48 | m | 2 |
| 5 | 3.84 | m | 1 |
| 6 | 2.12 | m | 1 |
|   | 1.58 | m | 1 |
| 7 | 1.64 | m | 2 |
| 8 | 2.93 | br s | 1 |
| 9 | 1.58 | m | 2 |
| 10 | 4.26 | br s | 1 |
| 12 | 1.81 | s | 3 |
| 14, 15, 16 | 1.04 | s | 9 |
| 18 | 8.07 | s | 1 |
| 20 | 6.39 | s | 1 |
| 24, 25, 26 | 1.34 | s | 9 |
| 10' | 8.94 | br s | 1 |

$^a$δ ppm, relative to the residual proton in solvent DMSO-d$_6$ at 2.49 ppm
$^b$The very broad singlet at δ 8.35 is from either H-2' or H-8'. One of these protons was not observed.
$^c$s = singlet, d = doublet, m = multiplet, br = broad $^{13}$C NMR Assignments of Compound I

| Assignment | Chemical Shift$^a$ | Multiplicity$^b$ |
|---|---|---|
| 1 | 171.2 | C |
| 2 | 51.7 | CH |
| 3 | 25.9 | CH$_2$ |
| 4 | 43.1 | CH$_2$ |
| 5 | 52.5 | CH |
| 6 | 21.3 | CH$_2$ |
| 7 | 32.2 | CH$_2$ |
| 8 | 46.5 | CH |
| 9 | 35.5 | CH$_2$ |
| 10 | 47.7 | CH |
| 11 | 168.5 | C |
| 12 | 23.3 | CH$_3$ |
| 13 | 50.7 | C |
| 14, 15, 16 | 29.3 | CH$_3$ |
| 17 | 148.8$^c$ | C |
| 18 | 152.9 | CH |
| 19 | 148.7$^c$ | C |
| 20 | 92.3 | CH |
| 21 | 167.3 | C |
| 22 | 32.6 | C |
| 23, 24, 25 | 30.0 | CH$_3$ |

$^a$δ ppm, relative to DMSO-d$_6$ at 39.5 ppm
$^b$Multiplicity was obtained from DEPT-135 spectrum
$^c$Assignments may be reversed Example 6

Preparation of Compound 6

Z-ASP-OBL

Compound 14a

5% Pd/Al$_2$O, Et$_3$SiH
MeCN

Compound 6

Step 1 Preparation of Compound 14a

Neat 1-Methylimidazole (3.0 equiv.) was added to an ice-cooled clear colorless solution of TCFH (1.25 equiv.) in acetonitrile (10 mL/g Z-ASP-OBL). Cooling was discontinued and the resulting clear solution was allowed to warm to 20° C. Solid Z-ASP-OBL (1.0 equiv.) was added to the stirred solution in a single portion, and the resulting clear colorless to faint yellow solution was stirred at 20° C. for 1 h. Neat 1-dodecanethiol (1.05 equiv.) was added in a single portion and the reaction mixture was stirred until complete as judged by HPLC. The reaction mixture was cooled to an internal temperature of 12° C. and water (0.02 mL/g Z-ASP-OBL) was added. The thin suspension was stirred for 1-2 h, then a solution of 50/50 acetonitrile-water (10 mL/g Z-ASP-OBL) was added to the reaction mixture resulting in a thick suspension of white solid. The suspension was stirred at 12° C. for 2 h, then the solid product was collected by filtration, washed with 50/50 acetonitrile-water and dried in a drying oven to give compound 14a as a white solid in 85% yield.

$^1$H NMR (500 MHz, CHLOROFORM-d) δ 7.39-7.26 (m, 10H), 5.72 (br d, J=8.2 Hz, 1H), 5.21-5.07 (m, 4H), 4.65 (dt,

J=8.2, 4.4 Hz, 1H), 3.30-3.06 (m, 2H), 2.83 (t, J=7.5 Hz, 2H), 1.63 (br s, 1H), 1.51 (quin, J=7.3 Hz, 2H), 1.37-1.20 (m, 19H), 0.88 (t, J=6.9 Hz, 3H)

$^{13}$CNMR (126 MHz, CHLOROFORM-d) δ 196.9, 170.4, 155.9, 136.2, 135.2, 128.6, 128.5, 128.4, 128.3, 128.2, 128.1, 67.6, 67.1, 50.9, 45.2, 31.9, 29.6, 29.5, 29.2, 29.2, 22.7, 14.1

Step 2 Preparation of Compound 6

Solid 5% Pd/Al$_2$O$_3$ (4 wt % relative to compound 14a) was charged to a reaction flask under nitrogen. In a separate flask, compound 14a (limiting reagent, 1.0 Equiv.) was combined with acetonitrile (3.7 mL/g relative to compound 14a) and the mixture stirred under a homogenous solution resulted. The solution was sparged by bubbling N2 through the solution for 15 minutes at room temperature. The solution was added to the catalyst in the flask and the mixture was stirred at room temperature (22-23° C.). Neat triethylsilane (1.15 equiv.) was added dropwise to the mixture over 5 minutes and the reaction mixture stirred until compound 14a was consumed as judged by HPLC analysis. The catalyst was then removed by filtration and the catalyst bed was washed with 1 mL/g acetonitrile. The filtrate was then extracted with twice with n-heptane (4 mL/g). In a separate flask, sodium bisulfite (0.48 g/g compound 14a) was combined with water (6.0 mL/g compound 14a) and the mixture stirred until a homogenous solution resulted. The product stream was diluted with methyl tert-butyl ether (4.0 mL/g) and the sodium bisulfite solution was added to the product solution and the biphasic mixture stirred vigorously until compound 6 was not detected in the organic phase. The phases were separated and the aqueous product stream extracted twice more with methyl tert-butyl ether (4.0 mL/g compound 14a). The aqueous product solution was cooled to 5° C.

In a separate flask, disodium hydrogenphosphate (0.2 g/g compound 14a) and monosodium phosphate (0.16 g/g compound 14a) were dissolved in water (1.0 mL/g/compound 14a). This solution was added to the 5° C. aqueous product solution such that the internal temperature remained below 10° C. Methyl tert-butyl ether (10 mL/g compound 14a) was added and the biphasic mixture stirred vigorously. A commercial 37 wt % solution of formaldehyde (0.6 g/g compound 14a) was then added to the biphasic mixture at 5° C. The reaction mixture as stirred at 5° C. until the bisulfite adduct of compound 6 was not detected in the aqueous phase by HPLC. The phases were separated and the organic product stream was washed with 5% aqueous sodium chloride (3.0 mL/g compound 14a) solution twice. The organic product phase was concentrated to a final volume of 2.0 mL/g compound 14a. n-Heptane (8.0 mL/g compound 14a) was added to the 20° C. product solution in MTBE to crystallize the product. The solid compound 6 was collected by filtration and washed with n-heptane (2.0 mL/g). The solid was dried at 40° C. The isolated yield was 65%.

$^1$H NMR (500 MHz, CHLOROFORM-d) δ 9.68 (s, 1H), 7.43-7.24 (m, 11H), 5.71 (br d, J=7.9 Hz, 1H), 5.27-5.01 (m, 4H), 4.68 (dt, J=8.2, 4.4 Hz, 1H), 3.17-3.08 (m, 1H), 3.07-2.98 (m, 1H).

$^{13}$CNMR (126 MHz, CHLOROFORM-d) δ 199.1, 170.5, 155.9, 136.1, 135.0, 128.6, 128.6, 128.3, 128.2, 128.1, 67.7, 67.2, 49.2, 45.8.

Preparation of Compound 6—Alternate Procedure

Compound 14a (13.48 g, 24.88 mmol, 100.0 mass %) dissolved in acetonitrile (50 mL, 252 mmol, 99.9 mass %) in a 250 mL single necked round bottomed flask.

Solid 5% Pd/C (651 mg, 0.30586 mmol, 5 mass %) was charged to a 100 mL stainless steel hydrogenation vessel and the vessel sealed up. The prepared compound 14a solution was charged to the vessel under nitrogen. Neat triethylsilane (8.2 mL, 50 mmol, 99 mass %) was added over 1 min under nitrogen, then the vessel was sealed. The reaction was allowed to stir for 4 h.

The reaction mixture was removed from the reactor and filtered through a 0.45 um PTFE filter. The solid in the filter was rinsed with acetonitrile (25 mL, 126 mmol, 99.9 mass %). The combined filtrate was biphasic having a dark colored phase that settled to the bottom of the flask.

The biphasic product stream was well mixed and 55 mL heptane were added. The jacket was set at 20° C. and the biphasic mixture agitated for 15 minutes. The phases were allowed to separate and the bottom acetonitrile phase was clear and colorless. The top phase was dark burnt orange color.

Pressure was reduced to 60 torr and distillation began immediately. The internal temperature dropped to 13-14° C., so the jacket temperature was increased to 25° C. Once the landmark of 21 mL was reached, 50 mL toluene were added by vacuum transfer. The pressure was reduced to 25 torr; jacket temperature was adjusted to 35° C. and the internal temperature started at 11-12° C. The internal temperature increased to 29.5° C. Once the distillation was complete, the jacket was set at 40° C. and cyclohexane (21 mL, 194 mmol, 99.9 mass %) was added. Solid compound 6 (100 mg, 0.2783 mmol, 95.00 mass %) was added in a single portion. The batch was held at 40° C. jacket temperature for 1 h, then cooled to 20° C. over 2 h and held at 20° C. overnight.

The mixture was a suspension of white solid. Neat cyclohexane (21 mL, 194 mmol, 99.9 mass %) was added to the suspension via syringe pump over 2 h and the suspension stirred for 5 h at 20° C. The solid product was collected on a 55 mm Whatman #1 filter paper. The mother liquor was recycled to the rinse out the reactor, then the cake was washed with 20 mL cyclohexane. The cake was air dried for 15 minutes, before transfer to a 20° C. drying oven to dry over the weekend to give 5.6 g, 62.7% yield of compound 6.

We claim:

1. A process for the preparation of a compound of formula (I):

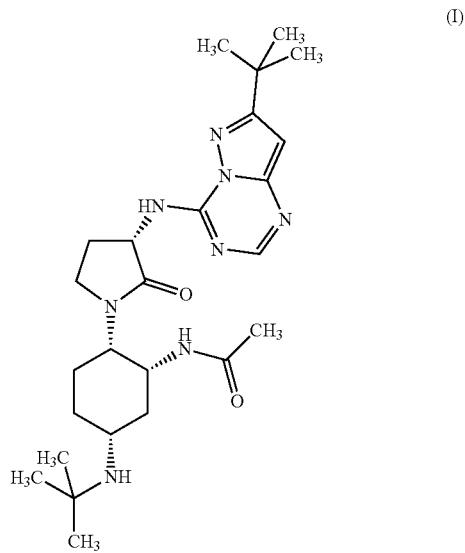 [SMILES: CC(=O)N[C@@H]1C[C@H](NC(C)(C)C)CC[C@@H]1N1CC[C@H](Nc2ncnc3cc(C(C)(C)C)nn23)C1=O]

wherein the process comprises the following steps:
a) reacting Compound 1 of the formula:

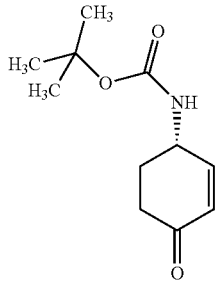

Compound 1 with a Compound 2 of the formula:

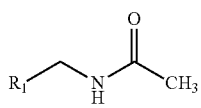

Compound 2 wherein:
R₁ is halogen or OC(O)CH₃;
in the presence of an acid and a solvent, to afford Compound 3 of the formula:

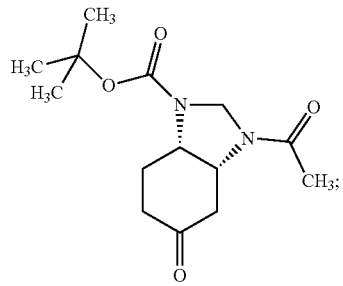

Compound 3 b) reacting Compound 3 above with a compound of the formula:

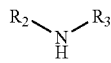

wherein:
R₂ is H or $C_1$-$C_6$ alkyl; and
R₃ is H or $C_1$-$C_6$ alkyl;
in the presence of a Lewis acid, followed by (a) sodium borohydride, (b) Pt/Al in the presence of hydrogen gas, or (c) Pd/C in the presence of hydrogen gas, to afford Compound 4 of the formula:

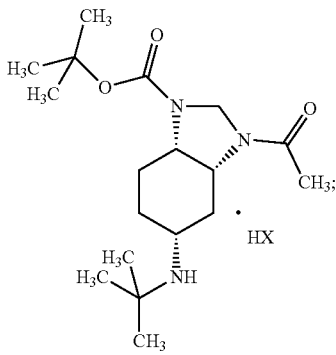

Compound 4 wherein:
X is halogen, sulfate, tartrate, or citrate;
c) reacting Compound 4 above with (a) sodium hydroxide, followed by methanesulfonic acid, in the presence of dichloromethane, or (b) sulfuric acid in the presence of isopropyl alcohol, to afford Compound 5 of the formula:

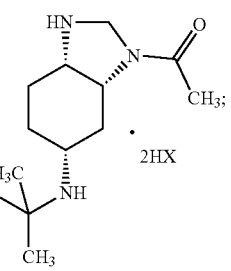

Compound 5 wherein:
X is halogen, sulfate, tartrate, or citrate;
d) reacting Compound 5 above with Compound 6 of the formula:

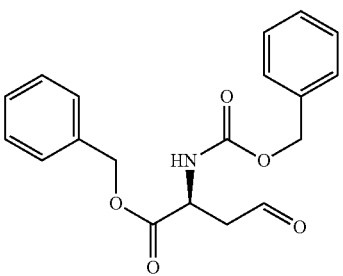

Compound 6 in the presence of triacetoxyborohydride and a solvent, to afford Compound 7 of the formula:

Compound 7

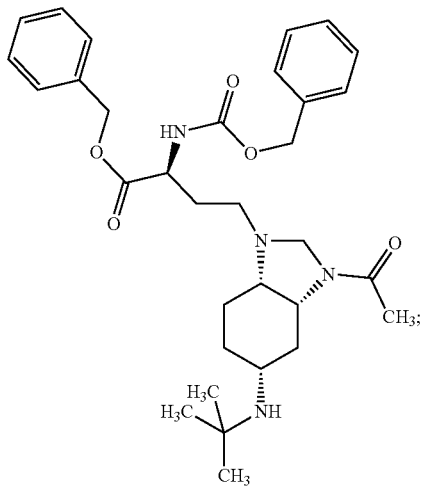

e) reacting Compound 7 above with an acid, in the presence of hydroxylamine, or a salt thereof, and a solvent, to afford Compound 8 of the formula:

Compound 8

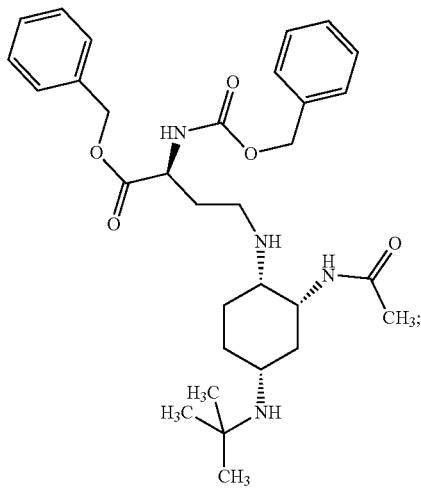

f) reacting Compound 8 above with an acid or a base, followed by heating the reaction mixture to a temperature in the range of 45° C.-70° C., in the presence of a solvent or solvent mixture, to afford Compound 9 of the formula:

Compound 9

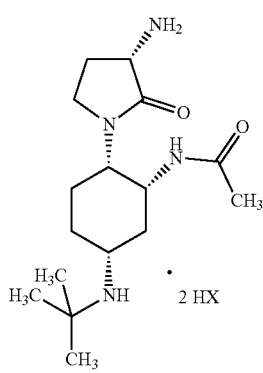

g) reacting Compound 9 above with Pd/C in the presence of hydrogen gas, followed by an acid, to afford Compound 10 of the formula:

Compound 10

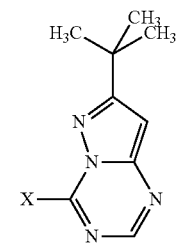

· 2 HX wherein:
  X is halogen; and
h) reacting Compound 10 above with Compound 11a of the formula:

Compound 11a wherein:
  X is halogen, 1-methylimidazole, or OR; and
  R is alkyl, aryl, a phosphate ester, or a sulfate ester;
in the presence of a solvent or solvent mixture, to afford the compound of formula (I) above.

* * * * *